(12) United States Patent
Reed et al.

(10) Patent No.: US 7,001,326 B2
(45) Date of Patent: Feb. 21, 2006

(54) DEVICE FOR LOADING RADIOACTIVE SEEDS

(76) Inventors: Jay C. Reed, 1304 Bradley La., Elk Grove Village, IL (US) 60007; Kevin M. Helle, 249 Remington Dr., Bartlett, IL (US) 60103

( * ) Notice: Subject to any disclaimer, the term of this patent is extended or adjusted under 35 U.S.C. 154(b) by 16 days.

(21) Appl. No.: 10/715,030

(22) Filed: Nov. 17, 2003

(65) Prior Publication Data

US 2005/0209500 A1 Sep. 22, 2005

Related U.S. Application Data

(63) Continuation of application No. 09/992,204, filed on Nov. 14, 2001, now Pat. No. 6,669,622, which is a continuation-in-part of application No. 09/712,563, filed on Nov. 14, 2000.

(51) Int. Cl.
*A61M 36/00* (2006.01)
(52) U.S. Cl. .......................................................... 600/7
(58) Field of Classification Search .............. 600/1–8; 604/19–21
See application file for complete search history.

(56) References Cited

U.S. PATENT DOCUMENTS

| | | | |
|---|---|---|---|
| 4,167,179 A | 9/1979 | Kirsch | |
| 4,402,308 A | 9/1983 | Scott | |
| 4,759,345 A | 7/1988 | Mistry | |
| 5,242,373 A | 9/1993 | Scott et al. | |
| 5,860,909 A | 1/1999 | Mick et al. | |
| 5,906,574 A | 5/1999 | Kan | |
| 5,928,130 A | 7/1999 | Schmidt | |
| 6,113,529 A | 9/2000 | Shi | |
| 6,213,932 B1 | 4/2001 | Schmidt | |
| 6,221,003 B1 | 4/2001 | Sierocuk et al. | |
| 6,267,718 B1 | 7/2001 | Vitali et al. | |
| 6,358,195 B1 | 3/2002 | Green et al. | |
| 6,530,875 B1 * | 3/2003 | Taylor et al. ................... | 600/7 |

FOREIGN PATENT DOCUMENTS

| | | |
|---|---|---|
| WO | WO00/61229 | 10/2000 |
| WO | WO01/66185 | 9/2001 |

* cited by examiner

*Primary Examiner*—John P. Lacyk
(74) *Attorney, Agent, or Firm*—Robert F. Chisholm

(57) ABSTRACT

A loader device, for dispensing implantation seeds from a seed magazine, comprising a body (3), seed magazine receiving and locating means (27), seed dispensing means (37) for ejecting seeds from a seed magazine, and a seed-transporting path (17) leading to a dispensing outlet (8), which loader device further comprises a spacer-transporting path (29, 31, 33, 35) for transporting spacers through the device to the dispensing outlet (8).

5 Claims, 7 Drawing Sheets

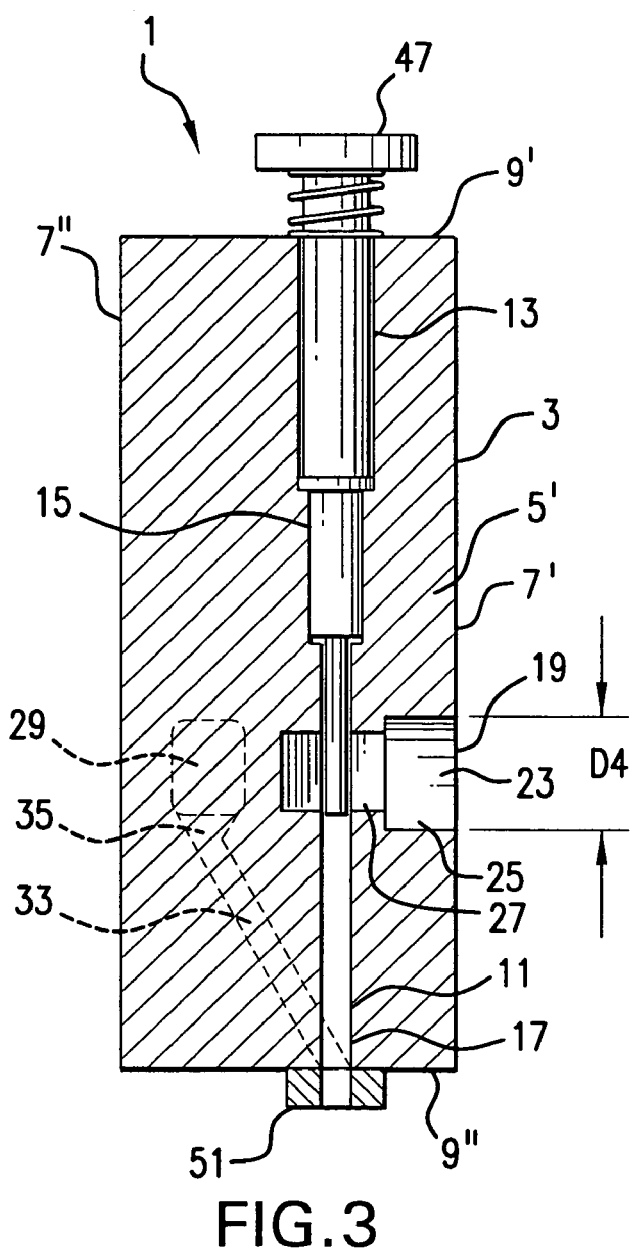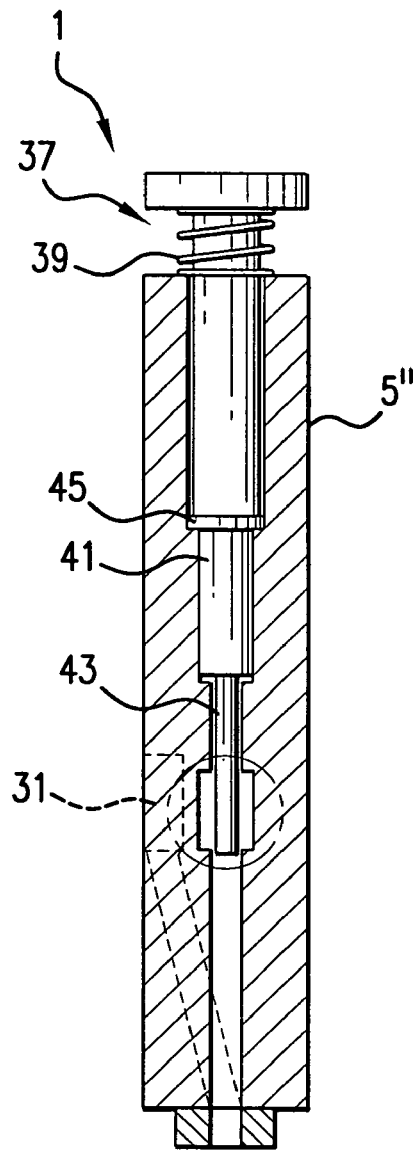
FIG.3
FIG.4

DEVICE FOR LOADING RADIOACTIVE SEEDS

This application is a continuation of U.S. application Ser. No. 09/992,204 filed Nov. 14, 2001, now U.S. Pat. No. 6,669,622 which is a continuation-in-part of U.S. application Ser. No. 09/712,563, filed Nov. 14, 2000, the entire disclosures of which are incorporated by reference herein.

FIELD OF THE INVENTION

The present invention relates to devices for loading radioactive seeds and optionally spacers into needles, catheters or other means, prior to administration to a patient.

BACKGROUND OF INVENTION

The treatment of prostrate cancers by brachytherapy, i.e. the permanent implantation of radioactive sources (known as "seeds") into a patient's body, involves the administration of typically 80–100 seeds per patient in a defined 3-D array. These seeds can be implanted by two different methods. In the first method, known from U.S. Pat. No. 5,242,373, a seed plug is assembled by hand from alternating loose seeds and biodegradable spacers (e.g. made of catgut) picked from a dish. The spacers can have any desired length and are positioned between the seeds in order to give the required separation between the seeds. The assembled plug is then implanted into the patient via a needle. A problem with this method is the person making the plug is exposed to radiation from the loose seeds in the dish and is also exposed to radiation when loading the seeds into the implantation needle. A further disadvantage is that considerable numbers of seeds and spacers have to be handled individually and each configured in the correct orientation to give the desired end-to-end "plug". The seed/spacers are also small e.g. typically 4–6 mm long, and this leads to time-consuming manual handling, with an associated radiation dose hazard. However this method has the advantage that as several seeds can be implanted in the patient at once through using pre-made plugs, the time spent in the operating theatre is reduced and the spatial separation of the seeds can be checked before implanting. A further problem with this method is that it requires the use of spacers. Spacers which are supplied loose suffer from the problems that they often have uneven, i.e. inconsistent lengths, they can have frayed ends, they swell if exposed to high humidity, they can pick up static charges if dry, they are not easy to see and their properties vary between suppliers.

In the second method, known from U.S. Pat. No. 5,860,909, individual seeds are implanted one at a time through a needle that is retracted in small steps out of the patient's tissue, with a seed being deposited in the tissue after each retraction step. No spacers are required in this method as the spacing between the seeds is determined by the amount by which the needle is retracted after each seed is deposited. A commonly used device for performing the second method is called a "Mick Applicator™". In order to facilitate the handling of the individual seeds for use in a "Mick Applicator™", a plurality of seeds can be supplied pre-packaged in a plastic or stainless steel magazine called a "Mick Cartridge™". This method exposes the operator to less radiation, as the magazines provide substantial radiation shielding except directly in front of the opening in the front of the magazine. However this method has the disadvantage that the time spent in the operating theatre is longer than for the first method as each seed is individually implanted and the needle must be retracted a precise distance before the next seed is implanted. Additionally, it is difficult to confirm the spatial separation between the seeds. It is an object of the present invention to overcome some of the problems associated with the prior art methods and devices for implanting seeds.

SUMMARY OF INVENTION

According to the present invention, at least some of the problems with the prior art devices and methods for loading seed implant needles are solved by means of a loader device of the instant invention and the methods for using such devices to load seed implant needles. The device and its use makes it possible for an operator to quickly, easily and accurately prepare loaded seed needles for implantation while being exposed to a minimum dose of radiation.

The device desirably incorporates a spacer magazine which has the advantages that spacers are protected by the magazine, and the fact that a spacer fits into the spacer magazine is a guarantee that it fulfils at least some of the dimensional requirements placed on a spacer, i.e. it has a length less than the maximum permitted length and a diameter less than the maximum permitted diameter. The spacers are desirably biodegradable spacers and made of a synthetic, bioabsorbable material. The spacers in the spacer magazine are desirably sterile. Similarly, the seed magazine desirably contains seeds which are sterile and within sterile integrity packaging.

The present invention provides a loader device for loading seeds and spacers into a container. The loader includes a loader body defining a channel network including an elongate seed passageway, an elongate spacer passageway, and a dispenser passageway. The seed and spacer passageways extend respectively in fluid communication between a first open end and a first end of the dispenser passageway. The loader body also defines a dispense port in fluid communication with the dispense passageway. The loader body further defines a seed cartridge port for receiving a seed cartridge having a seed dispense port. The loader body includes means for aligning and positioning the seed dispense port in registry with one open end of the seed passageway. A spacer port is also provided in fluid communication with one end of the spacer passageway. A seed plunger causes dispensement of a seed from the seed cartridge into the open end of the seed passageway, whereby a seed dispensed from said seed cartridge passes through the seed passageway to the dispenser passageway.

The loader body may further define a spacer cartridge port for receiving a spacer cartridge having a spacer dispense port. The loader body would include means for aligning and positioning the spacer dispense port in registry with one open end of the spacer passageway. A spacer plunger causes dispensement of a spacer from the spacer cartridge into the open end of the spacer passageway, whereby a spacer dispensed from the spacer cartridge passes through the spacer passageway to the dispenser passageway.

The dispense port may further be defined by a container adaptor for removably receiving a container for accepting the seeds and the spacers passed into the dispenser passageway. The container may take the form of any useful holder for seeds or spacers including, for example, an elongate hollow needle. The loader body may further comprise a transparent window defining at least a portion of the channel network so as to allow visualization of the seeds and the spacers passed into the dispenser passageway.

The loader of the present invention may further comprise a releasable blocking means selectively positionable within the dispenser passageway. The releasable blocking means may be moved between a first position preventing the passage of any seeds and spacers within the dispenser passageway through said dispense port and a second position allowing passage of any seeds and spacers within the dispenser passageway through the dispense port. The combination of the window with a releasable blocking means allows a user to visually verify the proper order of an array of seeds and spacers prior to loading same into a hollow needle.

The present invention further contemplates providing a stand assembly for maintaining the loader body in an orientation permitting gravity-assisted passage of seeds and spacers through the dispense port. The stand assembly would also permit a user to load seeds and spacers without having to support the loader device themselves. The stand assembly includes a base member and an elongate leg member extending between the base member and the loader body. The stand assembly may further include a shield member movably mounted with respect to the leg member between a first position extending between a user and a container mounted to the container adaptor and a second position allowing a user access to the container mounted to the container adaptor. The stand assembly may further include a spillage retaining cup positioned on the base member in underlying registry with the dispense port or a container mounted on the loader so as to catch and retain any seeds or spacers inadvertently released from the loader or the container.

The present invention further provides a loader device for loading seeds and spacers into a container comprising a loader body defining a Y-shaped channel network opening at a dispenser port. One leg of the channel network includes a seed passageway extending between a seed insertion port and a dispenser passageway. The other leg of the channel network includes a spacer passageway extending between a spacer insertion port and the dispenser passageway. The dispenser port defines an open end of the dispenser passageway. The loader body may further define a container adaptor about the dispenser port for removably receiving a container for the seeds and spacers passing through channel network.

The present invention further provides a method for loading seeds and spacers comprising the steps of (i) providing a loader with a body, seed magazine receiving and locating means, seed dispensing means for ejecting seeds from a seed magazine, a seed-transporting path leading to a dispensing outlet, and a spacer-transporting path leading to a dispensing outlet, (ii) mounting a seed magazine containing one or more seeds in the seed transporting path and dispensing a seed through the dispensing outlet, (iii) placing a spacer in the spacer transporting path; and (iv) dispensing the spacer through the outlet. The method may further provide (v) providing said loader with a spacer magazine receiving and locating means, (vi) mounting a spacer magazine containing spacers in the spacer magazine receiving and locating means, (viii) ejecting a spacer into the spacer transporting path, and (ix) dispensing the spacer through the dispensing outlet.

BRIEF DESCRIPTION OF THE FIGURES

FIG. 3 shows a view from the front of the loader device of FIG. 1 in a second state;

FIG. 4 shows a lateral view of the device of FIG. 3;

DETAILED DESCRIPTION OF INVENTION

Figure 1:
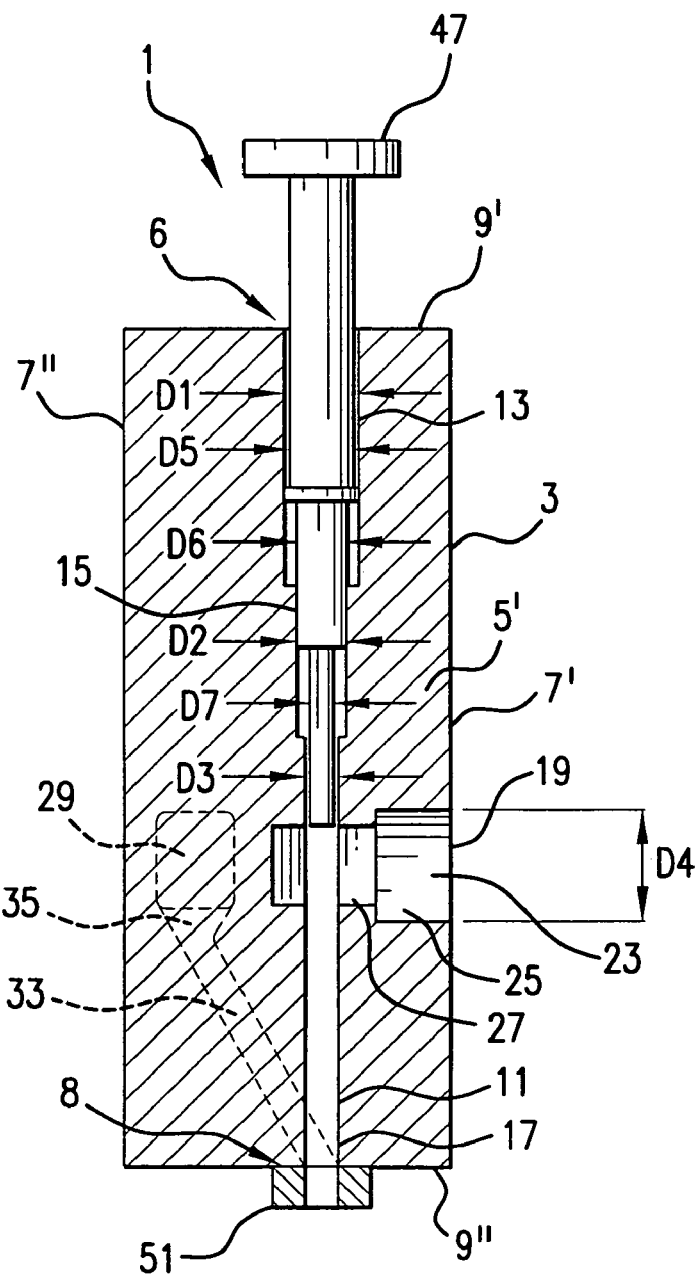
FIG. 1 shows a view from the front of one embodiment of a loader device in accordance with the present invention in a first state.
Figure 2:
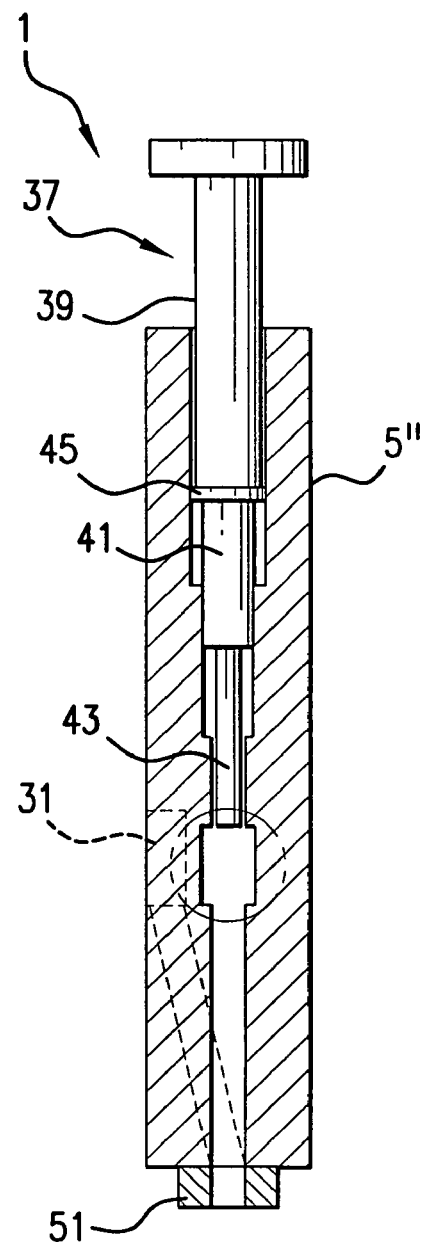
FIG. 2 shows a lateral view of the device of FIG. 1.

FIGS. 1 and 2 show a frontal view, resp. a lateral view of an embodiment of loader device 1 in accordance with the present invention. These figures are not to scale, internal features being shown unproportionally large in order to aid the clarity of illustration. The loader in accordance with the present invention is intended to facilitate the preparation of seed implant needles and is not intended to be used for the direct administration of seeds to a patient. Loader 1 has an elongated body 3 with a front and a rear wide face 5', resp 5", a first and a second short face 7', resp. 7", and upper and lower end faces 9', resp. 9". Body 3 is provided with a longitudinal through hole 11 that extends from an opening 6 in the surface of the upper end face 9' to a dispensing outlet 8 on the lower end face 9" and which has stepped diameters D1, D2, D3. The diameter D1 of through hole 11 is greatest in its upper portion 13 which extends from the upper end face 9' to an intermediate portion 15 that starts approximately one third of the distance down through hole 11. The intermediate portion 15 has an intermediate diameter D2 and extends from the lower end of upper portion 13 to approximately one half of the distance down through hole 11. The diameter D3 of through hole 11 is narrowest in the lower portion 17 that extends from the lower end of intermediate portion 15 to lower end face 9". Lower portion 17 is intended to act as a seed-transporting path for guiding seeds to the dispensing outlet 8. Note that any mentions of direction in this description refer to a frame of reference where the loader 1 is in its desired operating orientation in which the upper end face 9' is uppermost and the loader held substantially vertically.

Body 3 is made of a radiation shielding material of a suitable thickness to shield an operator from radiation emitted by radioactive seeds contained within it. Body 3 is provided with a lateral opening 19 on a first short face 7'. This opening 19 leads to a recess 23 adapted to receive a standard seed magazine (not shown). Recess 23 comprises a first cylindrical portion 25 with a diameter D4 adapted to receive the body of a seed magazine, and a rectangular portion 27 adapted to receive and retain the rectangular locating arms of a seed magazine. Rectangular portion 27 intersects through hole 11 approximately one third of the distance from the lower end face 9". The lengths and orientations of cylindrical portion 25 and rectangular portion 27 are adapted so that when a seed magazine is inserted fully into recess 23 then the seed-dispensing hole in the seed magazine (described below) is aligned with through hole 11.

The front wide face 5' is provided with a spacer-transporting path in the form of a spacer inlet opening 29 leading to a spacer receiving recess 31 that is connected by a internal chute 33 to the outlet 8 of through hole 11. Opening 29 is sufficiently large that a spacer (not shown) can be easily loaded into the recess 31. The bottom portion 35 of spacer receiving recess 31 is desirably funnel-shaped in order to facilitate the entry of spacers into chute 33. The diameter of chute 33 is greater than the diameter of a spacer so that spacers can be transported through chute 33 to outlet 8.

Through hole 11 can receive seed dispensing means such as a stepped cylindrical plunger 37, shown in a raised position in FIGS. 1 and 2. Plunger 37 has an upper portion 39 with a diameter D5 less than D1 and greater than D2, and a length which is the same as or greater than the length of through hole upper portion 13. Upper portion 39 is connected to a concentric intermediate portion 41 with a diameter D6 which is less than D2 and greater than D3, and a length which is approximately the same as or greater than the length of through hole intermediate portion 15. Intermediate portion 41 is connected to a concentric lower portion 43 with a diameter D7 that is less than D3 and less than the diameter of the seed-dispensing hole in the seed magazine. Lower portion 43 has a length which is approximately the same as or greater than the distance from the bottom of through hole intermediate portion 15 to the bottom surface of rectangular portion 27. The lengths of the plunger portions 39, 41, 43 and through hole portions 13, 15, 17 can be varied as desired, the only requirement is that they should make it possible to retract the plunger 37 to a seed loading upper position where lower plunger portion 43 is above the seed-dispensing hole of a seed magazine positioned in recess 23, as shown in FIGS. 1 and 2 and they also should make it possible to depress plunger 37 to a dispensing lower position in which lower plunger portion 43 extends through the seed-dispensing hole of a seed magazine positioned in recess 23, as shown in FIG. 3. This makes it possible to push any seed that is positioned in the seed dispensing hole down into the through hole 11 where it then falls to, and through, outlet 8. Plunger 37 is desirably provided with a sealing means 45 such as an O-ring to prevent unwanted material entering the lower portions of through hole 11. The upper end of plunger 37 can be provided with a actuating surface 47 which has a larger surface area than plunger upper portion 39, and which can be used to lift and depress plunger 37. If desired, plunger 37 can be provided with resilient means such as a spring 49, which biases plunger 37 to the upper loading position.

The lower end of through hole is provided with adapter means such as a threaded boss 51 or a Luer needle fitting or the like, that implantation needles or a capsule or other container can be attached to. It is also conceivable to provide universal adapters.

Figure 6:
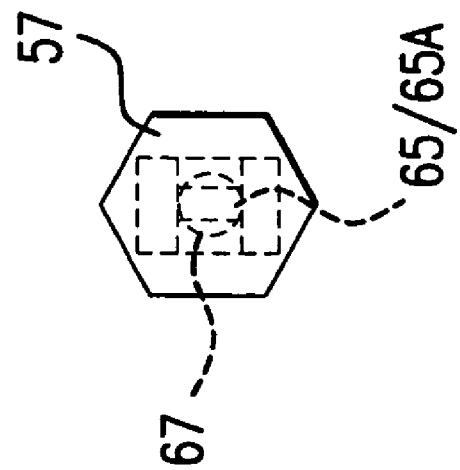
FIG. 6 shows a view from the end of the magazine of FIG. 5.
Figure 5:
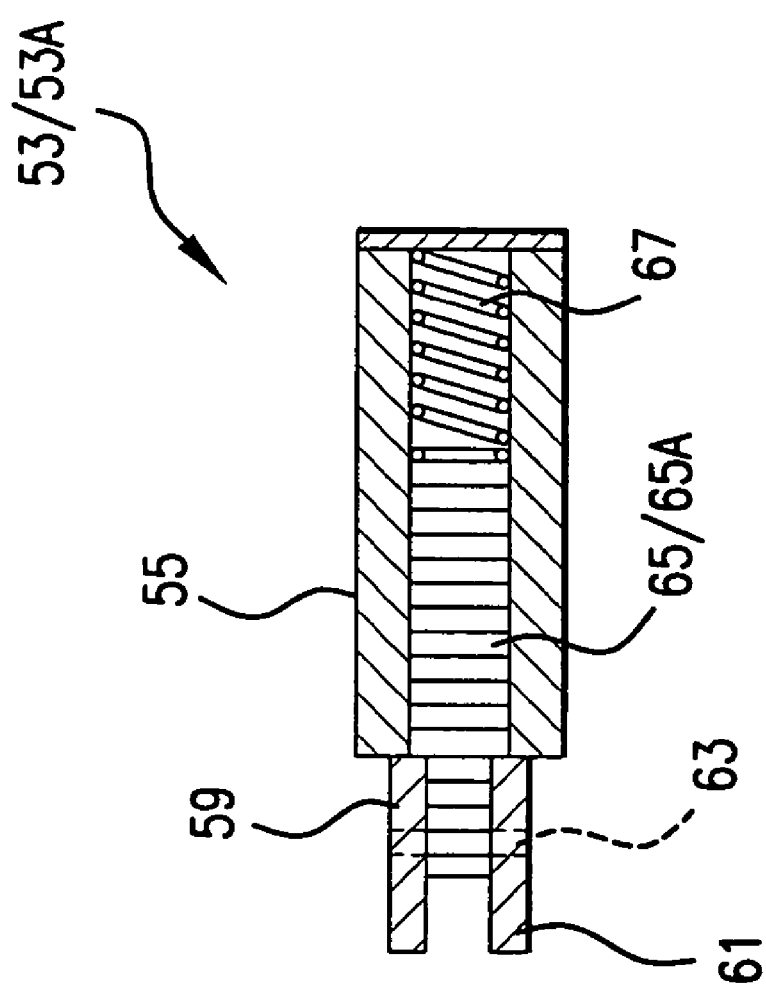
FIG. 5 shows a lateral view of an embodiment of a magazine suitable for use with a loader device in accordance with the present invention.

FIGS. 5 and 6 show side and end views respectively of a seed magazine 53 or spacer magazine 53A that can be fitted into a loader in accordance with the present invention. Magazine 53/53A has an elongated, hollow body 55 with a hexagonal cross-section. Other cross-sectional shapes are also possible, e.g. circular, square, oval, etc. When used for containing radioactive seeds, the body 55 is desirably made of a material with radiation shielding properties such as leaded plastic, stainless steel, lead glass, lead, tungsten, etc A first, loading end of the body is closed by a removable end plate 57, while the other end is provided with a seed- or spacer-dispensing outlet 59 arranged between two longitudinally projecting locating arms 61. The outlet 59 comprises a vertical seed-dispensing hole 63 bored through the locating arms 61. Seeds 65 or spacers 65A are arranged in a row inside the magazine 53/53A and pushed towards the hole 63 by resilient means such as a spring 67 inside the magazine 53/53A. The force provided by the spring 67 is sufficiently high that the friction between the wall of the hole 63 and a terminal seed 65 or spacer 65A in the hole 63 is enough to prevent the seed 65 or spacer 65A from falling out of the hole 63 under the influence of gravity.

Desirably, a magazine 53A used for spacers is filled with spacers 65A, desirably made of a synthetic, bioabsorbable material. Prior art spacers have been made of catgut—a material of animal origin that is undesirable from a regulatory and customer acceptability standpoint. An example of such a synthetic, bioabsorbable material is Vicryl™ that is made of approximately 90% polyglycollic acid and 10% polyactic acid. The spacer material is also desirably resistant to the temperatures used for heat sterilisation by autoclaving or dry heat sterilisation. Spacers 65A can be supplied sterile in a sterile magazine 53A in a sterile-integrity packaging material such as Tyvek™. The sterilisation can be performed in any suitable way, e.g. by heating or exposure to ethylene oxide gas (in which case a gas permeable packaging material is necessary if the sterilisation occurs after a magazine has been packaged), depending on the composition of the spacers used. The use of prepacked, sterile spacers has the advantage that the operator does not need to load his own magazines 53A with spacers 65A nor does he need to spend time sterilising the spacers before use. This ensures that sterile spacers are used.

Similarly, seeds 65 can also be supplied sterile and preloaded in a magazine for seeds 53. This magazine 53 can be supplied sterile in a sterile-integrity packaging material such as Tyvek™. The seeds and magazine can be sterilised in any suitable way, for example, in the ways mentioned above with respect to spacers 65A in a spacer magazine. Desirably a variety of pack sizes can be provided, e.g. packs containing a magazine 53 loaded with 5 seeds 65, or 10 seeds or 15 seeds, etc.

The use of a loader in accordance with the present invention for loading an implantation needle will now be illustrated. An operator holds the loader 1 in an upright position or places it in a stand in an upright position. A seed magazine 53 containing seeds 65 is inserted through opening 21 until the seed-dispensing hole 63 in the magazine is aligned with through hole 11. Although not shown, loader 1 desirably has locking means such as a locking detent for releasably retaining a magazine 53 in this position. An implantation needle is then attached to adapter means 51. In order to prevent the seeds and spacers from falling out of the bottom end of the needle, the bottom end of the needle can be provided with removable closing means such as a plug or an end cap. The plunger 37 is then depressed by the operator to its lower, seed-dispensing position. As the plunger 37 is depressed, lower plunger portion 43 passes through seed-dispensing hole 63 in the magazine 53 and pushes a seed 65 out of the magazine 53 and into the lower through hole portion 17. As the diameter of lower through hole portion 17 is greater than the diameter of the seed, the seed falls freely through the through hole 11 and out of its lower end, through adapter 51 and into the needle. The plunger 37 is then lifted to its upper, loading position. As the lower plunger portion 43 passes back up through the seed-dispensing 63 hole of the magazine 53, a new seed 65 is loaded into the seed-dispensing hole by the resilient means 67 of the magazine 53. The operator then places a spacer 65A of the desired dimensions into spacer receiving recess 31 and releases the spacer 65A. The spacer 65A falls down the internal chute 33, which has a diameter greater than the diameter of the spacer and enters the needle via adapter 51. This procedure is repeated until the desired number of seeds and spacers have been loaded into the needle. The needle can then be removed from adapter 51 and used or stored for later use. The procedure can be repeated for all the needles required for the treatment.

The use of a loader in accordance with the present invention for forming a seed plug will now be illustrated. An operator holds the loader 1 in an upright position or places it in a stand in an upright position. A seed magazine containing seeds 53 is inserted through opening 21 until the seed-dispensing hole in the magazine is aligned with through hole 11. A seed plug container is then attached to adapter means 51.

This container is desirably transparent in order to allow the operator to check that the loading is proceeding without problem and to allow checking of the number of seeds and their spacing. In order to shield an operator from radiation, the transparent container and any other transparent parts of a device in accordance with the present invention, as described later, are desirably made of a radiation attenuating transparent material such as leaded acrylic. In order to facilitate checking the number of seeds and their spacing, the container is desirably provided with graduated marks. In order to prevent the seeds falling out of the bottom end of the container, the bottom end of the container is provided with a removable plug or sealed in some other way. The plunger 37 is then depressed by the operator to its lower, seed-dispensing position and, just as in the previous example, a seed is fed into the container. The operator then places a spacer 65A of the desired length into spacer receiving recess 31 and releases the spacer 65A. The space falls down the internal chute 33, which has a diameter greater than the diameter of the spacer 65A and enters the container via adapter 51. This procedure is repeated until the desired number of seeds 65 and spacers 65A have been loaded into the container that can then be removed from adapter 51 and used or stored for later use.

In the event that the operator wishes to remove a seed 65 from the seed 30 magazine 53 in order to, for example, measure its radioactivity, then a seed magazine 65 can be attached as normal, any suitable container placed under the loader 1 and a seed 65 ejected into the container by depressing plunger 37.

Figure 7:
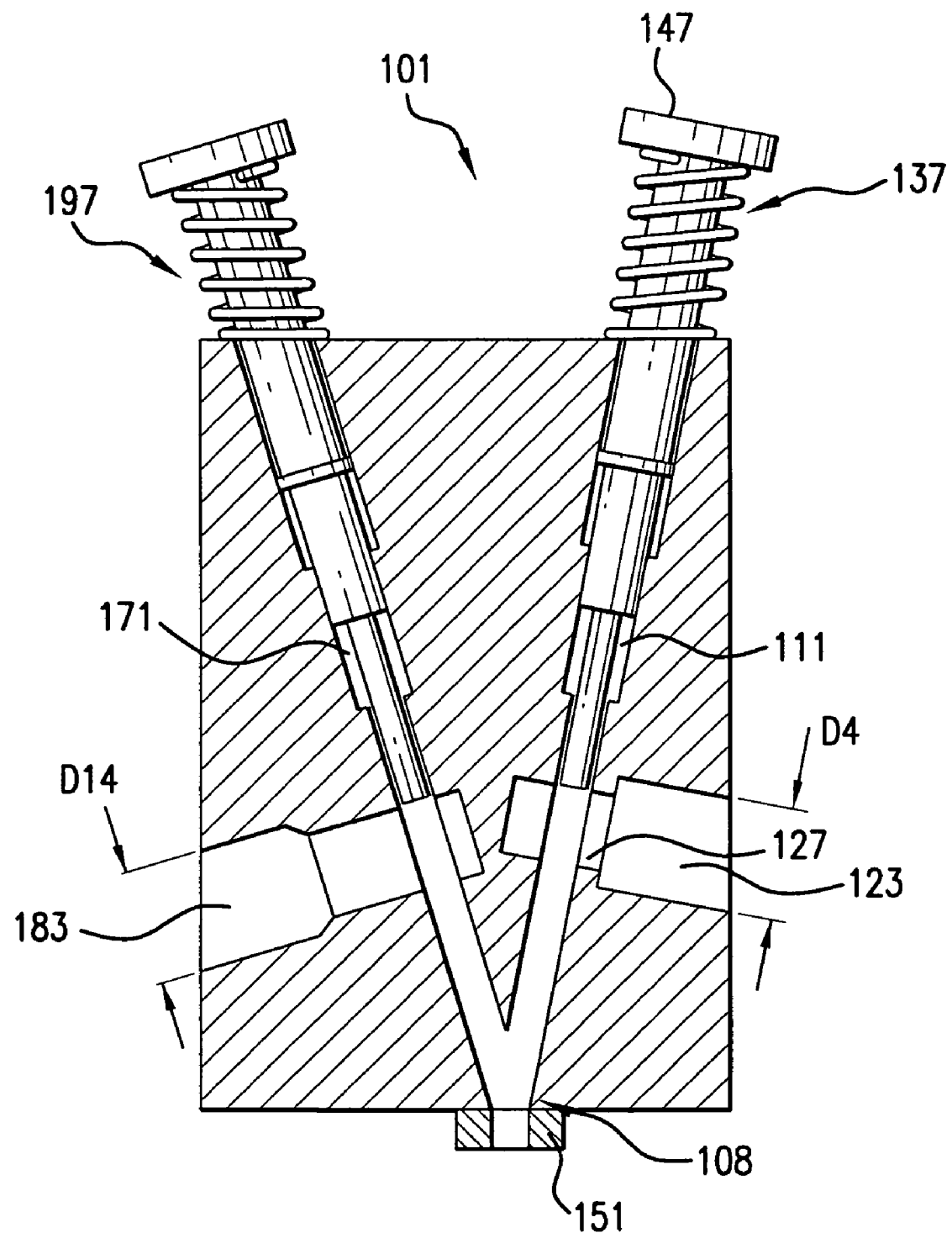
FIG. 7 shows a view from the front of a second embodiment of the present invention.

FIG. 7 shows a second embodiment of a loader 101 in accordance with the present invention. For the sake of brevity, many features have a function similar to that of the first embodiment of the present invention and will not be described for this embodiment. In this embodiment, the loader is provided with a first, seed dispensing means such as a plunger 137 and a second, spacer-dispensing means such as a plunger 197 and first and second magazine receiving recesses 123, resp. 183. First magazine receiving recess 123 is adapted to receive and retain a seed magazine 53, while second magazine receiving recess 183 is adapted to receive and retain a spacer magazine 53A. As mentioned above, spacer magazine 53A contains pre-cut spacers 65A and works in a similar way to a seed magazine 53. Desirably the magazine is sterile and the contents of the magazine are sterile before being put into the magazine. It is furthermore desirable that loaded and empty magazines and the loader can be sterilised, for example, by heating in an autoclave. In order to avoid confusion, seed magazines and spacer magazines can have different shapes or sizes, this is a desirred situation, especially as spacers 65A and seeds 65 often have different lengths, e.g. spacers 65A can be 5.5 mm long whiles seeds 65 can be 4.5 mm long. Alternatively, in the interests of economy it is possible to use the same magazines for seeds and spacers, in which case it is desirable to have different colours or other markings to avoid confusion. In any case it can be useful to have different colours for the different types of magazines, e.g. spacers could be supplied in a white magazine and seeds in a blue magazine. If different shaped or sized magazines are used then the diameters D4, resp. D14 of the first and second magazine receiving recesses and/or the shapes of these recesses should be correspondingly adapted in order to prevent the wrong type of magazine being retained in a recess.

First plunger 137 is movably fitted into a first stepped through-hole 111 which leads to an outlet 108 able to be fitted with an adapter 151 while second plunger 197 is movably fitted into a second stepped hole 171 which also leads to outlet 108. Loader 101 can be operated in a similar way to loader 1 except that with loader 101 spacers can be loaded by depressing plunger 167 instead of by loading individual spacers by hand through a spacer inlet opening.

Figure 8:
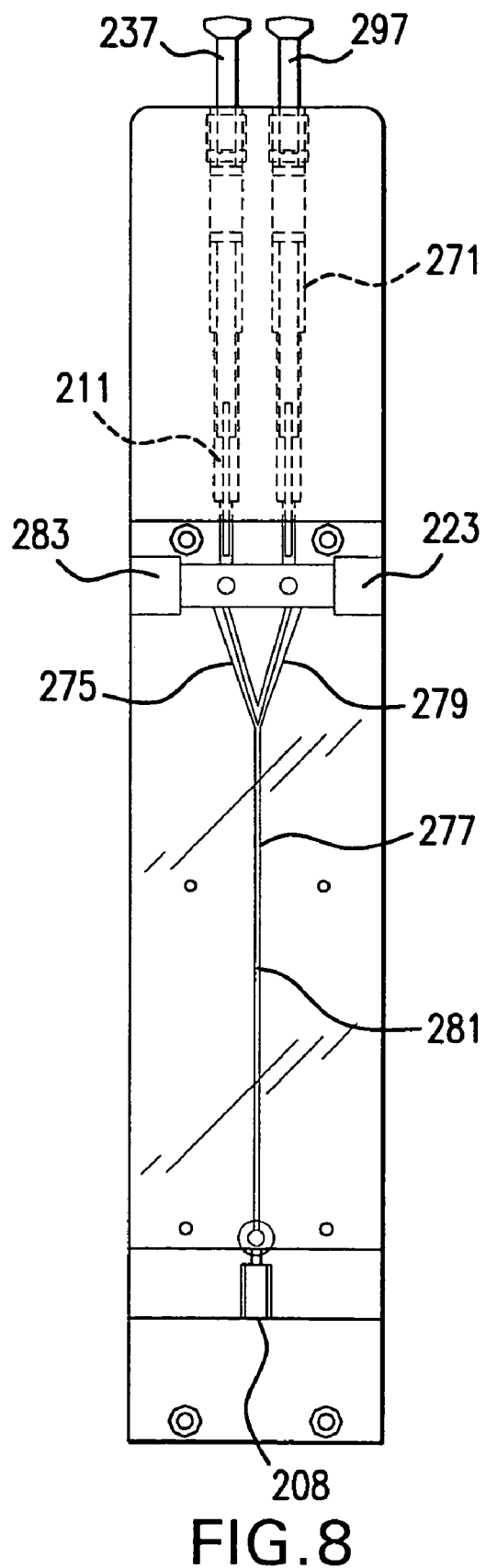
FIG. 8 shows a view from the front of a third embodiment of the present invention.
Figure 9:
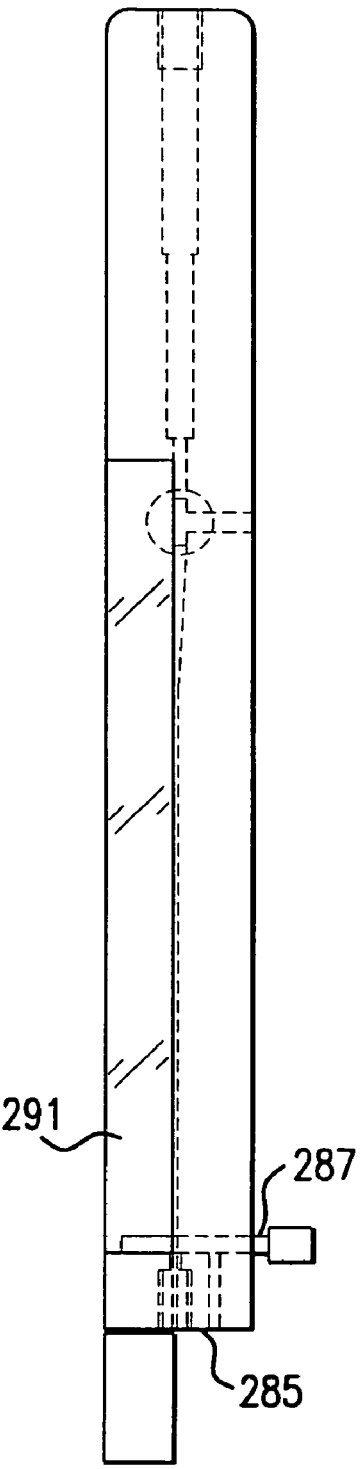
FIG. 9 shows a lateral view of the device of FIG. 8.

FIGS. 8 and 9 show a third embodiment of a loader 201 in accordance with the present invention. For the sake of brevity, many features have a function similar to that of the first and second embodiment of the present invention will not be described for this embodiment. For the sake of clarity of illustration, the hidden portions of plungers have been drawn with solid lines in FIG. 8 and the plungers omitted totally from FIG. 9. In this embodiment, the loader is provided with a first, seed dispensing means such as a plunger 237 and a second, spacer-dispensing means such as a plunger 297 and first and second magazine receiving recesses 223, resp. 283. First magazine receiving recess 223 is adapted to receive and retain a seed magazine 53, while second magazine receiving recess 283 is adapted to receive and retain a spacer magazine 53A. As mentioned before, in order to avoid confusion, seed magazines 53 and spacer magazines 53A can have different shapes or sizes or colours. First plunger 237 is in a first stepped through hole 211 which leads to the top of the first arm 275 of a Y-shaped channel 277, while second plunger 297 is in a second stepped hole 271 which leads to the top of the second arm 279 of the Y-shaped channel 277. The two arms 275, 279 of the Y-shaped channel meet at the top of the vertical leg 281 of the Y-shaped channel 277. The arms 275, 279 are desirably wider at the top and taper towards their intersection with leg 281. Arm 275 act as a seed-transporting path while arm 279 acts as a spacer-transporting path. Leg 281 extends down to an opening 208 in the bottom surface 285 of the loader. In order to prevent seeds 65 and spacers 65A from becoming jammed in the leg 281, the dimensions of leg 281 is desirably selected so that it is sufficiently narrow to preclude seeds and spacers from passing each other (or to begin passing each other). A removable blocking device such as a pin 287 is insertable in a hole 289 which extends from the rear surface of the loader towards the front of the loader and which intersects leg 281. When inserted into hole 289, this pin 287 prevents seeds and spacers in the leg 281 from passing. It is further conteplated that pin 287 may be a valve-type member that is spring biased to block leg 281. Upon overcoming a spring bias, pin 287 would provide an opening in fluid communication with leg 281 so as to allow a plug of seeds and spacers to pass. The front surface of loader 201 has a transparent portion 291, desirably made of radiation shielding material such as leaded acrylic, which allows an operator to see the contents of leg 281 while being shielded from radiation emitted by seeds in leg 281. This transparent portion 291 can be made quickly and easily removable in order to facilitate cleaning of the pathways, clearing foreign material or clearing any jammed seeds or spacers. In the event of a seed needing to be removed this rapid disassembly means that the operator is exposed to radiation from the seed for only a short time and therefore receives only a small dose of radiation. When forming a plug of seeds and spacers, the pin 287 is placed in the blocking position and the seeds and spacers dropped onto the pin 287, so that they gradually fill up the leg 281. The transparent portion 291 can be provided with graduation marks to aid checking the number of seeds and spacers in the device. The transparent portion 291 allows the operator to check the progress of the plug construction and, if the operator is interrupted when building a plug, it allows him to check on his return the status of the plug under construction. Non-standard arrangements of seeds and spacers, e.g. seeds separated by a variable number of spacers can also be validated visibly through transparent portion 291 before being loaded into a needle.

Loader 201 can be operated in a similar way to loader 101.

Figure 10:
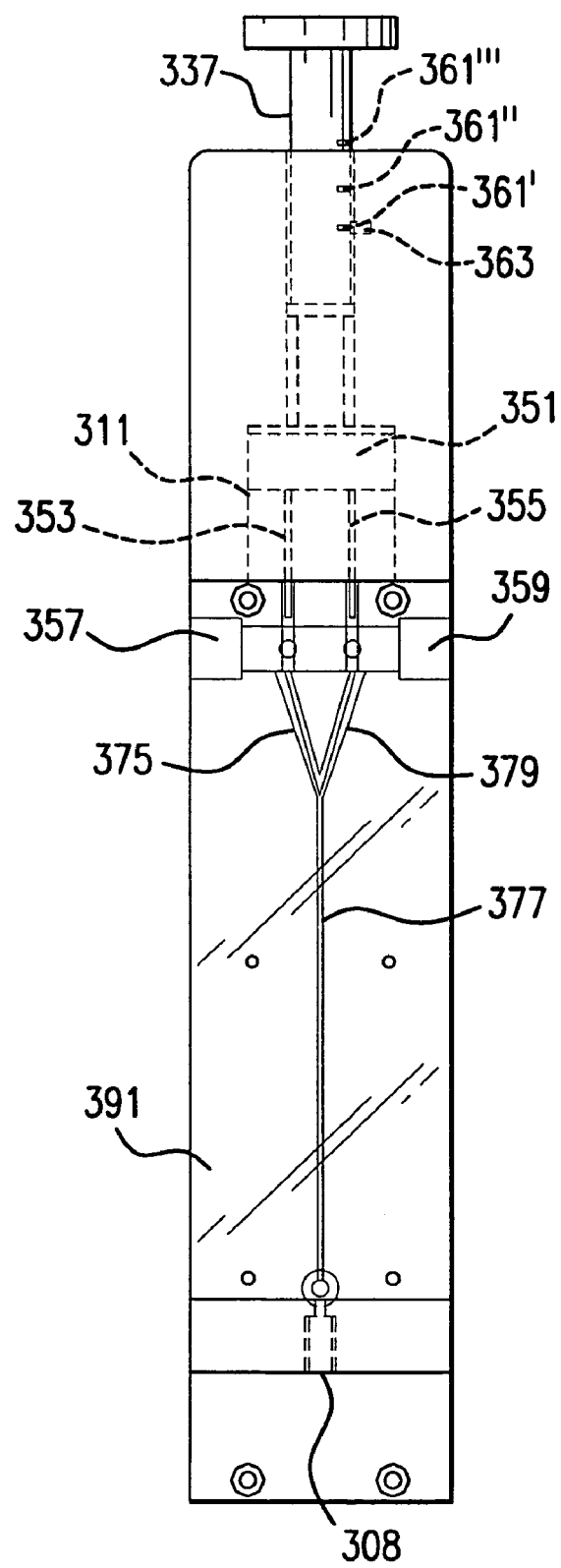
FIG. 10 shows a front view of a fourth embodiment of the present invention.

In a further embodiment of the invention, shown schematically in FIG. 10, a single plunger 337 is used to alternatingly load a spacer 65A and a seed 65. Plunger 337 is connected to a piston 351 which has two extensions 353, 355 which are aligned with the arms 375, 379 of a Y-shaped channel 377 which forms the seed and spacer transporting path. Extension 353 is shorter than extension 355. This means than when plunger 337 is depressed then extension 355 will pass through the magazine (not shown) in first magazine receiving port 359 before extension 353 passes through the magazine (not shown) in second magazine receiving port 357. Plunger 337 is provided with 3 recesses 361'–361''' that can co-operate with a spring-loaded indexing pin 363 on the inside of the hole 311 in which it is supported. The first recess 361' is aligned with the indexing pin 363 when neither extension is in line with the magazine receiving ports 357, 359. Second recess 361" is aligned with the indexing pin 363 when extension 355 has passed through the level of the magazine receiving ports 357, 359. Third recess 361''' is aligned with the indexing pin 363 when extension 353 has passed through the level of the magazine receiving ports 357, 359. An operator can load magazines onto this loader after raising plunger 337 until the first recess 361' is aligned with the indexing pin 363. Let us assume that the first magazine contains seeds and second magazine contains spacers. The operator can then eject a seed 65 from the first magazine by lowering plunger 337 until second recess 361" is aligned with the indexing pin 363. A spacer 65' can then be ejected by depressing plunger 337 until third recess 361''' is aligned with the indexing pin 363. If it is desired to eject a further spacer before ejecting a further seed then the plunger is lifted up until second recess 361" is aligned with the indexing pin 363 and then depressed again. If it is desired to load a seed then the plunger is lifted until first recess 361' is aligned with the indexing pin 363 and then lowered again until second recess 361" is aligned with the indexing pin 363.

Figure 11:
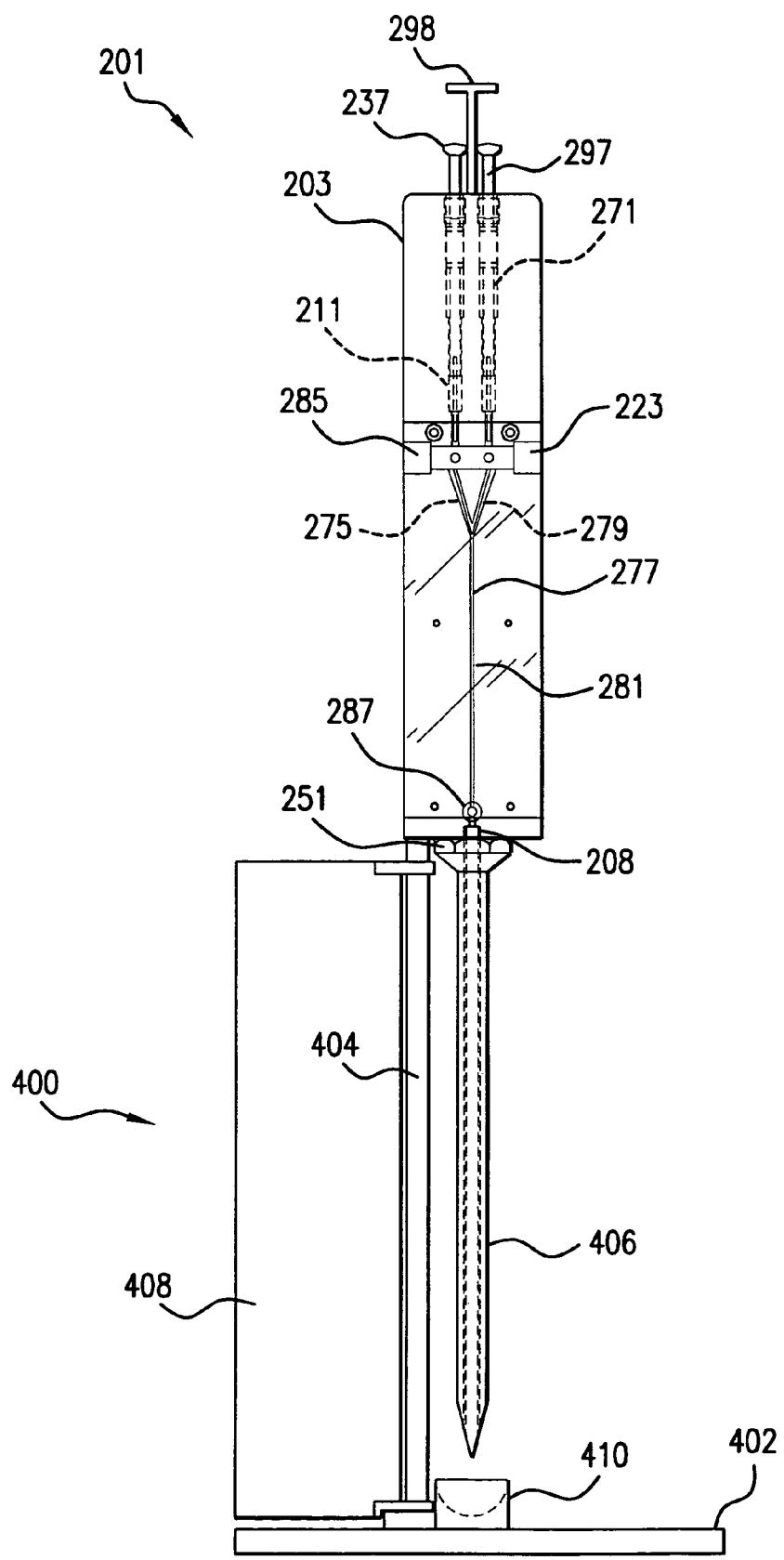
FIG. 11 shows a front view of a loader of the present invention with a stand assembly adaptable for use with any of the loaders of the present invention.

Referring now to FIG. 11, the present invention further provides a stand assembly 400 for a loader of the present invention. It will be recognized that stand assembly 400 may be employed with any of the loaders hereinabove described, but will be specifically discussed with respect to loader 201.

Stand assembly 400 is provided so as to maintain the elongated loader body of loader 201 in an orientation permitting gravity-assisted passage of seeds and spacers through dispense port 208. Stand assembly 400 includes base member 402 and elongate leg member 404 extending between base member 402 and the loader body of loader 201. An elongate hollow needle 406 is shown mounted to container adaptor 251 for receiving an ordered array of seed and spacers. As loader 201 is useful for loading radioactive seeds, an elongate planar shield member 408 is movably mounted with respect to leg member 404 for shielding a user from the radioactivity of the seeds dispensed into needle 406. Shield 408 is mounted so as to allow movement between a first position extending between a user and a container mounted to container adaptor 251 and a second position allowing a user access to the container mounted to container adaptor 251. Additionally, a spillage retaining cup 410 is positioned on base member 402 in underlying registry with dispense port 208. Cup 410 provides for catching and retaining any seeds or spacers passed through port 208 or through a container positoned on the loader that is inadvertently left open at its bottom aperture.

The loaders 1, 101, 201 in accordance with the present invention are desirably made from materials that provide screening against radioactivity, such as leaded plastic, stainless steel, lead glass, lead, tungsten, etc.

The above embodiments may be modified by providing separate dispensing outlets for seeds and spacers. These outlets can be connected by transparent tubes to a single needle or container, thus permitting both dispensing paths in the loader to be vertical and thereby reducing the risk of jamming occurring in the loader. The use of transparent tubes also makes it possible for the operator to check if any seeds or spacers have become jammed in the tubes. Moreover, FIG. 11 shows a divider 298 provided between plungers 237 and 297. A divider positioned so as to separate the adjacent plungers may further ensure that a user does not inadvertently depress the wrong plunger during dispense operations.

The above embodiments may also be modified by providing a device with a spacer magazine receiving port which is dimensioned so that, in the absence of a spacer magazine, an operator can by hand (preferably aided by forceps or the like) insert spacers into the port and drop them into the spacer transporting path. Alternatively the device could be provided with both a spacer magazine receiving port and a separate port for the manual introduction of spacers or other material into the spacer transporting path, so that an operator has the option of using a magazine or loading spacers or other material by hand. It is further contemplated that the seed magazine and the spacer magazine will include different mating geometries with the loader so that seeds will always be dispensed from one side of the loader and spacers always dispensed from the other side of the loader.

Additionally, a device in accordance with the present invention is readily adaptable for automation by providing plunger activation means which can be controlled by a computer or remotely by an operator. Suitable actuating means could be, for example, hydraulic or pneumatic actuators, or electrically powered actuators such as electric motors, linear actuators and the like. Additionally, magazine-changing means such as a robot arm could also be provided.

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. A method for dispensing seeds and spacers comprising the steps of:
   (i) providing a loader with a body, seed magazine receiving and locating means, seed dispensing means for ejecting seeds from a seed magazine, a seed-transporting path leading to a dispensing outlet, a spacer-transporting path distinct from said seed-transporting path, an elongate channel segment, and a dispensing outlet, wherein said elongate channel segment extends in fluid communication between both said seed-transporting path and said spacer-transporting path at one end and said dispensing outlet at the opposed end;
   (ii) mounting a seed magazine containing one or more seeds in said seed transporting path and dispensing a seed through said dispensing outlet;
   (iii) placing a spacer in said spacer transporting path; and
   (iv) dispensing said spacer through said outlet.

2. The method of claim 1, wherein said spacers are placed and dispensed by the method comprising:
   (i) providing said loader with a spacer magazine receiving and locating means;
   (ii) mounting a spacer magazine containing spacers in said spacer magazine receiving and locating means;
   (iii) ejecting a spacer into said spacer transporting path; and
   (iv) dispensing said spacer through said dispensing outlet.

3. The method of claim 2, wherein said spacers are made of a synthetic, bioabsorbable material.

4. The method of claim 3, wherein said spacers in said spacer magazine are sterile.

5. The method of claim 4, wherein said seed magazine contains seeds and said magazine and seeds are sterile and removed from sterile integrity packaging.

* * * * *